United States Patent
Krumbholz

(10) Patent No.: US 7,381,258 B2
(45) Date of Patent: Jun. 3, 2008

(54) OPAQUE DENTAL CERAMIC—METHOD OF PRODUCTION AND USE THEROF

(75) Inventor: Klaus Krumbholz, Langen (DE)

(73) Assignee: Degudent GmbH, Hanau (DE)

( * ) Notice: Subject to any disclaimer, the term of this patent is extended or adjusted under 35 U.S.C. 154(b) by 324 days.

(21) Appl. No.: 11/167,933

(22) Filed: Jun. 28, 2005

(65) Prior Publication Data

US 2005/0288165 A1 Dec. 29, 2005

(30) Foreign Application Priority Data

Jun. 28, 2004 (EP) .................................. 04015117

(51) Int. Cl.
*A61K 6/00* (2006.01)
(52) U.S. Cl. .............................. 106/35; 501/6; 501/10; 501/32; 501/59; 501/66; 501/67
(58) Field of Classification Search .................. 106/35; 501/6, 10, 32, 59, 66, 67
See application file for complete search history.

(56) References Cited

U.S. PATENT DOCUMENTS

| 4,671,770 | A | * | 6/1987 | Bell et al. .................... 433/223 |
| 5,432,130 | A | | 7/1995 | Rheinberger et al. |
| 5,698,019 | A | | 12/1997 | Frank et al. |
| 6,022,819 | A | | 2/2000 | Panzera et al. |
| 6,280,863 | B1 | | 8/2001 | Drescher et al. |
| 6,342,202 | B1 | | 1/2002 | Evans et al. |
| 2003/0122270 | A1 | | 7/2003 | Brodkin et al. |

FOREIGN PATENT DOCUMENTS

| DE | 19606492 | 8/1972 |
| DE | 4334493 | 3/1995 |
| WO | 2004000743 | 12/2003 |

* cited by examiner

*Primary Examiner*—C. Melissa Koslow
(74) *Attorney, Agent, or Firm*—Dennison, Schultz & MacDonald

(57) ABSTRACT

The invention relates to an opaque dental ceramic for burning on a rack or implant of dental restoration at least comprising $SiO_2$, $Al_2O_3$, $B_2O_3$, $Na_2O$, $K_2O$ as well as $TiO_2$. To cover the non-dental-coloured implant material sufficiently the invention provides that the opaque dental ceramic is clouded by precipitation of one or more crystalline $TiO_2$ phases.

12 Claims, No Drawings

OPAQUE DENTAL CERAMIC—METHOD OF PRODUCTION AND USE THEROF

FIELD OF THE INVENTION

The invention relates to an opaque dental ceramic for burning on a rack of dental restoration comprising at least $SiO_2$, $Al_2O_3$, $B_2O_3$, $Na_2O$, $K_2O$ as well as $TiO_2$. In particular the invention relates to a method of production for an opaque dental ceramic for branding on a rack or implant of dental restoration using at least $SiO_2$, $Al_2O_3$, $B_2O_3$, $Na_2O$, $K_2O$ as well as $TiO_2$ containing raw material composition, melting of the raw material composition, tempering of the melt in water, temperature treatment of the so obtained transparent glass frits and transfer of the temperature treated glass frits by grinding into a powder for application on the rack.

Further, the invention relates to the use of a frit according to the invention as opaque dental ceramic to face a rack of dental restoration.

DESCRIPTION OF RELATED ART

A dental ceramic restoration with a multi layered arrangement on top of a core is known from DE-A-43 34 493, which can be obtained by applying an opaque layer of the composition 50 to 60 weight % $SiO_2$, 4 to 10 weight % $Na_2O$, 0 to 2, 5 weight % CaO, 8 to 14 weight % $K_2O$, 10 to 20 weight % $Al_2O_3$, 0 to 6 weight % $B_2O_3$, 5 to 12 weight % $TiO_2$ as well a especially on oxide basis, on a core followed by burning of this arrangement.

In DE-A-43 34 493 a silica based material, suitable for burn up, of an easily flowing basic melt and an opaque fraction is suggested, which contains 38 to 42 weight % of the total mass and 10.4 to 11.5 weight % of $TiO_2$. Consequently, the burning temperature and the coefficient of thermal expansion are limited, thereby limiting the silica based material only for the facing of a limited number of compositions.

The main requirements for an opaque ceramic for the facing of dental restorations are as follows:
- The ceramic has to be enough opaque so that a rack or implant of non-dental-color is optically covered by burning on a layer of preferably not more than 0.2 mm thickness thereon,
- The burn temperature has to be harmonized with the other materials, whereby during branding on alloys the temperature should be preferably at least 100° C. under the solidus temperature of the alloy,
- A sufficient adhesion has to be achieved with the rack. This requires good coverage of the surface during branding on and a matching coefficient of thermal expansion.

Typically opaque materials are manufactured in practice as follows. One or more glass or leucite based frits are melted. After grinding of the frits a clouding agent as for example tin, zircon, or cerium oxide are admixed in a fraction up to 30 weight %. For achieving a homogenous dispersion of the clouding agent and to reduce separation these mixtures can be melted together in an additional step. Afterwards the enamel finely ground. By admixture of suitable pigments specific colors can be obtained.

However, known method do not allow to exploit the full potential of the clouding agent, since no homogenous dispersion of the clouding agent is achieved. Rather the particles of the clouding agent tend to conglomeration. Further, known methods do not allow that the clouding agent has an optimal particle size which should be within the wavelength of light, therefore be under 1 µm. Consequently an unnecessary large amount of cloudy agent is necessary without achieving the desired goal to achieve sufficient coverage of the rack or implant with a single application of opaque material. An additional disadvantage is that the high melting oxides, which are used as clouding agents, do not contribute to the coverage of the rack to be covered during burning on. Consequently insufficient adhesion may result which necessitates a primary brand with a better covering ceramic.

It is known from DE-A-43 34 493 a dental restoration which contains as only crystalline face leucite in a fraction of 20 to 45 weight %. Necessarily required components are 40 to 95 weight % $SiO_2$, 5 to 25 weight % $Al_2O_3$, 5 to 25 weight % $K_2O$. Further, optionally $TiO_2$ and $Na_2O$ can be present.

An opaque glass ceramic according to WO-A-2004/000743 is necessarily free of $TiO_2$.

According to EP-A-0 622 342 an opaque glass with a continuous glass face and a discontinuous glass face is suggested. The glass can contain as component $TiO_2$ in an amount which allows it to be dissolved, to avoid a clouding, since otherwise the desired opaqueness is covered.

In a dental ceramic according to US-A-2003/0122270 up to 2 weight % $TiO_2$ as well as F are present. Because of the low amount of $TiO_2$ this remains in solution. The presence of F allows for manufacture of a thin fluid enamel. Disadvantageously the manufacture leads to the mission of fluorine.

In DE-A-196 06 492 plastic covered dental artificial replacements as well as methods of their production are described. Between the rack and the outer plastic layer can be an adhesive which may contain $TiO_2$ as clouding agent.

SUMMARY OF THE INVENTION

According to one aspect of the present invention there is provided an opaque dental ceramic, a method of its production and use thereof which allows for a sufficient coverage of the non-dental-coloured rack without the application of several layers of opaque material. In addition an optimal particle size of the clouding agent should be achieved and conglomeration should be largely avoided. Also desired adaptation to the physical properties of the skeletal structure or implant, especially with respect to its thermal expansion and coverage should be achieved.

According to the present invention the underlying problem is solved substantially by an opaque dental ceramic which is clouded by precipitation of one or more crystalline phases of $TiO_2$. The precipitation of the crystalline phases is effected by tempering of the glass that is produced by frits. Tempering does not mean burning of the glass powder, that is the grounded frit on the rack or implant.

In other words an opaque dental ceramic is provided that has, based on the precipitation of at least one crystalline phase of $TiO_2$ (anatase and/or rutile), such intense opaqueness, that already a single application achieves a complete coverage of the color of the metallic or non metallic rack or implant as for example a crown or a dental bridge. The dental ceramic is dyed so that it can be used as basis for the desired dental color. The crystalline $TiO_2$ phases shall be saturated or loaded with coloring ions like chromium ions so that no further coloring ions can be taken up after application of the ceramic on the rack or implant to avoid undesired discolouring of the finished ceramic (facing).

In a preferred embodiment the dental ceramic comprises:

| | |
|---|---|
| SiO$_2$ | 44-54 weight-% |
| Al$_2$O$_3$ | 3-8 weight-% |
| B$_2$O$_3$ | 8-12 weight-% |
| P$_2$O$_5$ | 0-4 weight-% |
| Li$_2$O | 0-3 weight-% |
| Na$_2$O | 5-9 weight-% |
| K$_2$O | 5-9 weight-% |
| MgO | 0-2 weight-% |
| CaO | 0-4 weight-% |
| BaO | 0-3 weight-% |
| TiO$_2$ | 8-16 Weight-% |
| Colouring oxide | <0.2 weight-% |

Alternatively, there is provided a dental ceramic that contains:

| | |
|---|---|
| SiO$_2$ | 42-54 weight-% |
| Al$_2$O$_3$ | 5-10 weight-% |
| B$_2$O$_3$ | 2-10 weight-% |
| P$_2$O$_5$ | 0-4 weight-% |
| Li$_2$O | 0-2 weight-% |
| Na$_2$O | 4-11 weight-% |
| K$_2$O | 4-11 weight-% |
| MgO | 0-2 weight-% |
| CaO | 0-3 weight-% |
| BaO | 0-1 weight-% |
| TiO$_2$ | 12-20 weight-% |
| Colouring oxide | <0.2 weight-% | or

| | |
|---|---|
| SiO$_2$ | 36-50 weight-% |
| Al$_2$O$_3$ | 12-16 weight-% |
| B$_2$O$_3$ | 2-8 weight-% |
| P$_2$O$_5$ | 0-3 weight-% |
| Li$_2$O | 0-2 weight-% |
| Na$_2$O | 5-11 weight-% |
| K$_2$O | 7-12 weight-% |
| MgO | 0-2 weight-% |
| CaO | 0-3 weight-% |
| BaO | 0-1 weight-% |
| TiO$_2$ | 15-20 weight-% |
| Colouring oxide | <0.2 weight-% |

The total quantity of all components is 100 weight %.

To achieve a high coefficient of thermal expansion the dental ceramic can in addition contain crystalline leucite.

Independent of the above it is intended that the raw material of the dental ceramic according to the above composition(s) contains coloring oxides up to 0.2 weight %. Oxides can be iron, chromium, manganese and/or nickel. Additional components as for example ZnO, F, SnO$_3$, Sb$_2$O$_3$ and/or CeO$_2$ can also be added without disadvantage up to 2 weight %.

The dental ceramic according to the invention comprises a continuous face of glass at least with one discontinues crystal face (TiO$_2$). The crystal phase of TiO$_2$ is thereby separated by or loaded with coloured ions in such an amount that later discolouring of the dental ceramic applied to the rack or implant is avoided.

According to a further aspect of the present invention there is provided a method of producing an opaque dental ceramic for burning on a rack or implant of dental restoration by using a composition of raw material comprising SiO$_2$, Al$_2$O$_3$, B$_2$O$_3$, Na$_2$O, K$_2$O as well as TiO$_2$, melting at a transparent glass from the composition of raw material, tempering the melt in a liquid as water, temperature treatment of such obtained glass frit and transfer of the quenched glass frit by grinding into a powder which can be applied to a rack or implant. The glass can hereby be tempered at a temperature T of 700° C.≦T≦950° C. The tempering alone can be effected over a time of 30 min.≦t≦90 min.

DETAILED DESCRIPTION OF THE INVENTION

For the production of dental ceramic one or more frits of crystalline TiO$_2$ phases of the following composition of raw material can be used;

| | |
|---|---|
| SiO$_2$ | 44-54 Weight-% |
| Al$_2$O$_3$ | 3-8 Weight-% |
| B$_2$O$_3$ | 8-12 Weight-% |
| P$_2$O$_5$ | 0-4 Weight-% |
| Li$_2$O | 0-3 Weight-% |
| Na$_2$O | 5-9 Weight-% |
| K$_2$O | 5-9 Weight-% |
| MgO | 0-2 Weight-% |
| CaO | 0-4 Weight-% |
| BaO | 0-3 Weight-% |
| TiO$_2$ | 8-16 Weight-% |
| Colouring Oxide | <0.2 Weight-% | for setting up a frit of type A and/or

| | |
|---|---|
| SiO$_2$ | 42-54 Weight-% |
| Al$_2$O$_3$ | 5-10 Weight-% |
| B$_2$O$_3$ | 2-10 Weight-% |
| P$_2$O$_5$ | 0-4 Weight-% |
| Li$_2$O | 0-2 Weight-% |
| Na$_2$O | 4-11 Weight-% |
| K$_2$O | 4-11 Weight-% |
| MgO | 0-2 Weight-% |
| CaO | 0-3 Weight-% |
| BaO | 0-1 Weight-% |
| TiO$_2$ | 12-20 Weight-% |
| Colouring Oxide | <0.2 Weight-% | for setting up a frit of type B and/or

| | |
|---|---|
| SiO$_2$ | 36-50 Weight-% |
| Al$_2$O$_3$ | 12-16 Weight-% |
| B$_2$O$_3$ | 2-8 Weight-% |
| P$_2$O$_5$ | 0-3 Weight-% |
| Li$_2$O | 0-2 Weight-% |
| Na$_2$O | 5-11 Weight-% |
| K$_2$O | 7-12 Weight-% |
| MgO | 0-2 Weight-% |
| CaO | 0-3 Weight-% |
| BaO | 0-1 Weight-% |
| TiO$_2$ | 15-20 Weight-% |
| Colouring Oxide | <0.2 Weight-% | for setting up a frit of type C.

According to a preferred embodiment of the invention up to 0.2 weight % of the raw material can be added of one or more coloured oxides in form of oxides of iron, chromium, manganese, and/or nickel. In addition the raw material may contain as further components for example ZnO, F, SnO$_3$, Sb$_2$O$_3$ and/or CeO$_2$ up to 2 weight %.

To achieve a high thermal expansion coefficient of the opaque dental ceramic leucite can be crystallized in the glass melt.

The invention is based on the use of a frit of type A with the following composition:

| | |
|---|---|
| SiO$_2$ | 44-54 Weight-% |
| Al$_2$O$_3$ | 3-8 Weight-% |
| B$_2$O$_3$ | 8-12 Weight-% |
| P$_2$O$_5$ | 0-4 Weight-% |
| Li$_2$O | 0-3 Weight-% |
| Na$_2$O | 5-9 Weight-% |
| K$_2$O | 5-9 Weight-% |
| MgO | 0-2 Weight-% |
| CaO | 0-4 Weight-% |
| BaO | 0-3 Weight-% |
| TiO$_2$ | 8-16 Weight-% |
| Colouring Oxide | <0.2 Weight-% | and/or a frit of type B with the composition:

| | |
|---|---|
| SiO$_2$ | 42-54 Weight-% |
| Al$_2$O$_3$ | 5-10 Weight-% |
| B$_2$O$_3$ | 2-10 Weight-% |
| P$_2$O$_5$ | 0-4 Weight-% |
| Li$_2$O | 0-2 Weight-% |
| Na$_2$O | 4-11 Weight-% |
| K$_2$O | 4-11 Weight-% |
| MgO | 0-2 Weight-% |
| CaO | 0-3 Weight-% |
| BaO | 0-1 Weight-% |
| TiO$_2$ | 12-20 Weight-% |
| Colouring Oxide | <0.2 Weight-% | and/or a frit of type C with the composition:

| | |
|---|---|
| SiO$_2$ | 36-50 Weight-% |
| Al$_2$O$_3$ | 12-16 Weight-% |
| B$_2$O$_3$ | 2-8 Weight-% |
| P$_2$O$_5$ | 0-3 Weight-% |
| Li$_2$O | 0-2 Weight-% |
| Na$_2$O | 5-11 Weight-% |
| K$_2$O | 7-12 Weight-% |
| MgO | 0-2 Weight-% |
| CaO | 0-3 Weight-% |
| BaO | 0-1 Weight-% |
| TiO$_2$ | 15-20 Weight-% |
| Colouring Oxide | <0.2 Weight-% | wherein each frit contains one or more crystalline TiO$_2$ phases as opaque dental ceramic for facing a rack or implant for a dental restoration.

The total amount of components is 100 weight %.

The invention further provides the use of the frit of type A as matrix for facing a rack or implant of titanium or an alloy with titanium as principle component.

Further the use of type B as opaque matrix for facing oxide ceramic racks or implants is suggested.

In another embodiment the invention provides a frit of type C with crystallized leucite as matrix for a composition to be branded on.

According to yet a further embodiment according to the present invention there is provided the use of the frit of type C together with the frit of type A and/or a frit of the type B for facing a skeletal structure with a thermal expansion coefficient between 12.5 to 13.5×10$^{-6}$/K$_{(20°\ C.-400°\ C.)}$.

Preferably the frit of type A is used for burning temperatures T$_{B1}$≦820° C. and/or a coefficient of thermal expansion between 7 and 9×10$^{-6}$/K$_{(20°\ C.-400°\ C.)}$.

The frit of type B is especially intended for producing a dental ceramic with a burning temperature T$_{B2}$≦820° C. and/or a coefficient of thermal expansion between 8 and 11×10$^{-6}$/K$_{(20°\ C.-400°\ C.)}$.

The frit of type C with precipitation of leucite may be used as opaque dental ceramic with a coefficient of thermal expansion between 12.0 and 16.5×10$^{-6}$/K$_{(20°\ C.-400°\ C.)}$.

According to the invention there is provided an opaque dental ceramic for which one or more frits are used, the production comprises substantially the following steps:

Melting of a transparent glass of a TiO$_2$-containing composition of raw material, Fritting of the glass melt, Tempering of the glass produced through frits at a suitable temperature for recrystallization of TiO$_2$, and Grinding of semi crystalline glass frit(s) for transfer into an applicable powder.

According to the required properties the frits can be used alone or in admixture with other frits and/or additional clouding agents or pigments. Small amounts of coloured oxide fused into the glass result in the incorporation of these in the crystal leucite and thereby provide a suitable color with respect to the desired dental color.

The composition of glasses can be varied within wide ranges to adapt the ceramic to a wide spectrum of burn temperatures and thermal expansion. To achieve a high thermal expansion (high coefficient of thermal expansion) leucite (K$_2$O.Al203.4SiO2) can be crystallized besides one or more phases of TiO$_2$.

As mentioned above frits of type A are especially suitable for facing of a frame or implant made of titanium, while frits of type B, for example, can be used as opaque matrix for oxide ceramic frames or implants. Frits of type C have a high coefficient of thermal expansion (CTE) through the crystallization of leucite and are therefore suitable as matrix for compositions to be burned on. At a relatively high amount of K$_2$O a frit is obtained with a CTE of more than 14.0×10$^{-6}$/K$_{(20°\ C.-400°\ C.)}$. By admixture of a frit of type C with a frit of type A and/or a frit of type B a suitable CTE can be obtained, which for commercially available alloys is between 12.5 and 13.5×10$^{-6}$/K$_{(20°\ C.-400°\ C.)}$. At a relatively high amount of Al$_2$O$_3$ (more than 16 weight % based on the composition without the amount of TiO$_2$) can through reduction of the amount of K$_2$O a frit be produced which, without the admixture of a further frit, has the desired CTE.

By taking full advantage of the clouding agent in form of the crystalline TiO$_2$ phase(s) an optimal coverage of the metallic and non metallic rack, frame or implant is achieved, wherein through staining the basis for the desired dental color is achieved.

The clouding agent TiO$_2$ admixed to the composition of raw material of the frit and is dissolved completely in the flux of glass. In the subsequent process of tempering the clouding agent is precipitated in crystalline form and effective as clouding agent. Trough variation of the temperature conditions (temperature and/or time) as well as through suitable composition of the frit, the amount precipitated, modification and the size of the crystal can be effected.

The clouding by recrystallization of TiO$_2$ is especially suitable, since—in comparison to SnO$_2$—it is dissolved at high temperatures in large amounts in the glass melt and precipitated again in large amounts by lower temperatures. Furthermore the crystalline phases of Tio$_2$ have the highest index of refraction (rutile: n$_D$=2.76; n$_D$=2.52) of all common clouding agents and therefore maximum clouding effect.

Rutile crystallizes in needle like shapes, while anatase develops into pyramidal shaped crystals of a diameter of the grain under 1 μm.

The composition of the frit effects whether primarily rutile or anatase crystallizes.

In general, anatase and rutile will be present in a weight ratio 0:1≦anatase:rutile≦1:0, and preferably, 1:2≦anatase:rutile≦2:1.

While clouding by recrystallization of $TiO_2$ is known in enamel technology. However recrystallization takes place during burning on the enamel powder on the blank. In contrast re crystallization according to the invention takes place during a separate process step, namely tempering of the glass manufactured from the composition of raw materials. If on the other hand recrystallization would take place during burning on of the opaque layer on a rack or implant of dental restoration, no optimal rate of recrystallization would be achieved, since the burning temperature is different from the favourable temperatures for re crystallization. Further the burning time is too short for a maximal amount of precipitation.

It is known that an uncontrolled uptake of coloured cations, especially of ions of chromium happens in the crystal lattice of $TiO_2$, whereby an undesired discoloration of the white $TiO_2$ towards ocher takes place. Hereby rutile can take up more coloured oxides as anatase and this therefore more intensely coloured than the latter.

The same problem arises with the manufacture of dental restorations, for example through a composition to be covered or through admixed pigments which contain coloured oxides. To avoid these disadvantages there is provided according to the invention that selective colour oxides are added to the composition of raw materials, so that an uncontrolled up take of foreign ions does not lead to uncontrolled discolouring of the ceramic. For example selective admixture in amounts up to 0.2% of chromium-iron-aluminium-zinc-spinel, commercially available as a brown coloring agent, is possible such that a desired ocher color is achieved. This has the additional advantage that a suitable starting base for the aimed for dental color in comparison to the white of the uncoloured $TiO_2$ can be achieved. Further the amount of pigments in admixture, which can be more than 15 weight % for dark dental colors, can in such a way be strongly reduced.

It is advantageous to have beside the more intense coloured frit a white-coloured frit available. Thus, selected dental colours can be achieved through blending of both frits and if required by admixture of further pigments. As elucidated above, an intense colored frit is best achieved by rutile crystallization, while conditions for an anatase crystallization lead to a more light coloured frit.

Preferably the required pigments for achieving the desired dental color are incorporated during tempering of the frits. For example, manufacture of four different opaque materials of different color (for example light ocher, ocher, yellow ocher, grey brown) any desired dental color can be achieved by blending.

Further details, advantages and characteristics of the invention are not only shown in the claims, the characteristics inferred from them, but also from the following description of preferred exemplary embodiments.

Table 1 shows different raw material compositions of frits.

| | Example 1 | Example 2 | Example 3 | Example 4 |
|---|---|---|---|---|
| $SiO_2$ | 50.7 | 47.7 | 42.2 | 38.2 |
| $Al_2O_3$ | 5.5 | 7.8 | 14.8 | 14.7 |
| $B_2O_3$ | 9.5 | 4.9 | 4.5 | 6.8 |
| $P_2O_5$ | 3.3 | 2.0 | | 1.8 |
| $Li_2O$ | 1.9 | 0.7 | 0.8 | 0.9 |
| $Na_2O$ | 5.4 | 8.6 | 9.3 | 9.8 |
| $K_2O$ | 5.8 | 7.3 | 8.4 | 8.7 |
| CaO | 3.8 | 2.2 | 1 | 1 |
| BaO | 2 | | | |
| $TiO_2$ | 12 | 17.6 | 18 | 18 |
| $CeO_2$ | | 1.1 | | |
| MgO | | | 0.9 | |
| Coloring Oxides | 0.1 | 0.1 | 0.1 | 0.1 |

(data in weight %)

Example 1 belongs to type A of the above mentioned frits. As in the other examples raw materials feldspar, borax, titanium oxide as well as carbonates and nitrates of alkali and alkaline earth metals are used. The raw material is well mixed and melted at about 1,450° C. in a gas heated drop skillet oven or the like. The molten mass is collected in a water bath. The such obtained transparent frit is dried, coarsely ground, layered on chamotte plates or the like and tempered for approximately one hour by approximately 800° C. in an electric oven. The sintered frit material is again quenched in water, dried and ground to a fine powder, which after admixture with a liquid can be applied to a selected base.

The corresponding ceramic is opaque and because of the absence of coloured oxides only light cream-colored. The crystallization phase of the ceramic is primarily anatase. The coefficient of thermal expansion is $8.8 \times 10^{-6}/K_{(20° C.-400° C.)}$. The ceramic can for example be burned on a rack or implant of titanium for example at 760° C.

The composition shown in example 2 of table 1 corresponds to the frit of type B. The manufacture takes place similar to the one described for example 1, whereby however the melting temperature is raised to about 1500° C. and tempering takes place by 850° C. The ceramic such produced is opaque and ocher coloured. As crystal phases were determined anastase and rutile. The burn-on-temperature is about 860° C. and the CTE is $9.8 \times 10^{-6}/K$. The ceramic can for example be burned on a rack or implant of zirconium oxide.

The composition according to example 3 corresponds to the frit of type C. Manufacture takes place similar to the examples mentioned above. As crystal phases appear leucite and anatase. Through this the frit is only light cream-coloured. The CTE is $12.7 \times 10^{-6}/K$. The burn-on-temperature is about 860° C.

The composition according to example 4 corresponds to the frit of type C. The coefficient of thermal expansion is about $12.5 \times 10^{-6}/K$. The burn-on-temperature is about 860° C. The frit is because of the rutile crystallization and the presence of coloured oxides of intense ocher colour.

What is claimed is:

1. An opaque dental ceramic for burning on a rack or implant of a dental restoration, the opaque dental ceramic comprising $SiO_2$, $Al_2O_3$, $B_2O_3$, $Na_2O$, $K_2O$ and $TiO_2$,
   the opaque dental ceramic being clouded by precipitation of at least one crystalline phase of $TiO_2$ by tempering, the at least one crystalline phase of $TiO_2$ being sufficiently saturated with coloring ions that discoloration of the opaque dental ceramic after application of the ceramic to the rack is avoided.

2. The opaque dental ceramic according to claim 1, wherein the opaque dental ceramic comprises, by weight, 44-54% $SiO_2$, 3-8% $Al_2O_3$, 8-12% $B_2O_3$, 0-4% $P_2O_5$, 0-3% $Li_2O$, 5-9% $Na_2O$, 5-9% $k_2O$, 0-2% MgO, 0-4% CaO, 0-3% BaO, 8-16% $TiO_2$ and <0.2% coloring oxide.

3. The opaque dental ceramic according to claim 1, wherein the dental ceramic comprises, by weight, 42-54% $SiO_2$, 5-10% $Al_2O_3$, 2-10% $B_2O_3$, 0-4% $P_2O_5$, 0-2% $Li_2O$, 4-11% $Na_2O$, 4-11% $K_2O$, 0-2% MgO, 0-3% CaO, 0-1% BaO, 12-20% $TiO_2$ and <0.2% coloring oxide.

4. The opaque dental ceramic according to claim 1, wherein the opaque dental ceramic comprises, by weight, 36-50% $SiO_2$, 12-16% $Al_2O_3$, 2-8% $B_2O_3$, 0-3% $P_2O_5$, 0-2% $Li_2O$, 5-11% $Na_2O$, 7-12% $K_2O$, 0-2% MgO, 0-3% CaO, 0-1% BaO, 15-20% $TiO_2$ and <0.2% coloring oxide.

5. The opaque dental ceramic according to claim 1, additionally comprising crystalline leucite.

6. The opaque dental ceramic according to claim 1, additionally comprising up to 0.2 weight % of at least one coloring oxide selected from the group of oxides consisting iron, chromium, manganese and nickel.

7. The opaque dental ceramic according to claim 1, additionally comprising up to 2 weight % of at least one further component selected from the group consisting of ZnO, F, $SnO_2$, $Sb_2O_3$ and $CeO_2$.

8. The opaque dental ceramic according to claim 1, wherein the recrystallized $TiO_2$ comprises at least one of rutile and anatase.

9. The opaque dental ceramic according to claim 8, wherein the anatase and rutile are present in a weight ratio of $0:1 \leq$ anatase:rutile $\leq 1:0$.

10. The opaque dental ceramic according to claim 9, wherein the weight ratio is $1:2 \leq$ anatase:rutile $\leq 2:1$.

11. An opaque dental ceramic for burning on a rack or implant of a dental restoration, the opaque dental ceramic comprising by weight, 44-54% $SiO_2$, 3-8% $Al_2O_3$, 8-12% $B_2O_3$, 0-4% $P_2O_5$, 0-3% $Li_2O$, 5-9% $Na_2O$, 5-9% $k_2O$, 0-2% MgO, 0-4% CaO, 0-3% BaO, 8-16% $TiO_2$ and <0.2% coloring oxide, the opaque dental ceramic being clouded by precipitation of at least one crystalline phase of $TiO_2$ by tempering.

12. An opaque dental ceramic for burning on a rack or implant of a dental restoration, the opaque dental ceramic comprising $SiO_2$, $Al_2O_3$, $B_2O_3$, $Na_2O$, $K_2O$ and $TiO_2$, and additionally comprising crystalline leucite, the opaque dental ceramic being clouded by precipitation of at least one crystalline phase of $TiO_2$ by tempering.

* * * * *